US012588841B2

(12) United States Patent
Sun et al.

(10) Patent No.: US 12,588,841 B2
(45) **Date of Patent: *Mar. 31, 2026**

(54) CALIBRATION-FREE PULSE OXIMETRY

(71) Applicant: VIAVI Solutions Inc., San Jose, CA (US)

(72) Inventors: Lan Sun, Santa Rosa, CA (US); Chang Meng Hsiung, Redwood City, CA (US); Babs Soller, Carlsbad, CA (US)

(73) Assignee: VIAVI SOLUTIONS INC., Chandler, AZ (US)

( * ) Notice: Subject to any disclaimer, the term of this patent is extended or adjusted under 35 U.S.C. 154(b) by 890 days.

This patent is subject to a terminal disclaimer.

(21) Appl. No.: 17/661,306

(22) Filed: Apr. 29, 2022

(65) Prior Publication Data

US 2022/0248994 A1 Aug. 11, 2022

Related U.S. Application Data

(63) Continuation of application No. 16/780,412, filed on Feb. 3, 2020, now Pat. No. 11,331,017.

(Continued)

(51) Int. Cl.
A61B 5/1455 (2006.01)
A61B 5/024 (2006.01)

(52) U.S. Cl.
CPC ...... A61B 5/14552 (2013.01); A61B 5/02427 (2013.01)

(58) Field of Classification Search
CPC .................... A61B 5/14552; A61B 5/02427
See application file for complete search history.

(56) References Cited

U.S. PATENT DOCUMENTS 7,532,919 B2 5/2009 Soyemi et al.
10,542,894 B2 1/2020 Zhao et al.
(Continued)

FOREIGN PATENT DOCUMENTS

CN 104114089 A 10/2014
CN 107847158 A 3/2018
(Continued)

OTHER PUBLICATIONS

International Search Report and Written Opinion for Application No. PCT/US2020/017041, mailed on Apr. 16, 2020, 13 pages.
Stratonnikov A.A., et al., "Evaluation of Blood Oxygen Saturation in Vivo from Diffuse Reflectance Spectra," Journal of Biomedical Optics, Oct. 2001, vol. 6 (4), pp. 457-467.
(Continued)

*Primary Examiner* — Marjan Fardanesh
(74) *Attorney, Agent, or Firm* — FOLEY & LARDNER LLP

(57) ABSTRACT

A device may identify a peak timestamp and a trough timestamp based on a first principal component of photoplethysmography (PPG) data associated with a plurality of wavelength channels. The device may generate a peak absorption spectrum based on the peak timestamp and the PPG data, and may generate a trough absorption spectrum based on the trough timestamp and the PPG data. The device may determine a measured arterial blood spectrum based on the peak absorption spectrum and the trough absorption spectrum. The device may fit the arterial blood spectrum model to the measured arterial blood spectrum to determine a set of values, each value in the set of values corresponding to a variable in a set of variables. The device may calculate an arterial oxygen saturation value based on one or more values of the set of values.

20 Claims, 10 Drawing Sheets

Related U.S. Application Data

(60) Provisional application No. 62/805,173, filed on Feb. 13, 2019.

(56) References Cited

U.S. PATENT DOCUMENTS

| | | |
|---|---|---|
| 10,799,127 B2 | 10/2020 | Wei et al. |
| 2003/0055324 A1 | 3/2003 | Wasserman |
| 2010/0324384 A1 | 12/2010 | Moon et al. |
| 2011/0205535 A1 | 8/2011 | Soller et al. |
| 2012/0179011 A1 | 7/2012 | Moon et al. |
| 2014/0114151 A1 | 4/2014 | Miller |
| 2018/0214088 A1 | 8/2018 | Newberry |
| 2020/0253517 A1 | 8/2020 | Sun et al. |

FOREIGN PATENT DOCUMENTS

| | | |
|---|---|---|
| CN | 108042107 A | 5/2018 |
| CN | 108778105 A | 11/2018 |
| EP | 0555553 A2 | 8/1993 |
| WO | 9520757 A1 | 8/1995 |

OTHER PUBLICATIONS

Yang Y., et al., "Quantitative Measurement of Muscle Oxygen Saturation Without Influence from Skin and Fat Using Continuous-wave Near Infrared Spectroscopy," Optics Express, Oct. 17, 2007, vol. 15 (21), pp. 13715-13730.

Zou F., et al., "Investigation of Spectral Interferences on the Accuracy of Broadband CW-NIRS Tissue S02 Determination," Biomedical Optics Express, Oct. 1, 2010, vol. 1 (3), pp. 748-761.

Extended European Search Report on EP Application No. 25200370.2 dated Oct. 21, 2025 (9 pages).

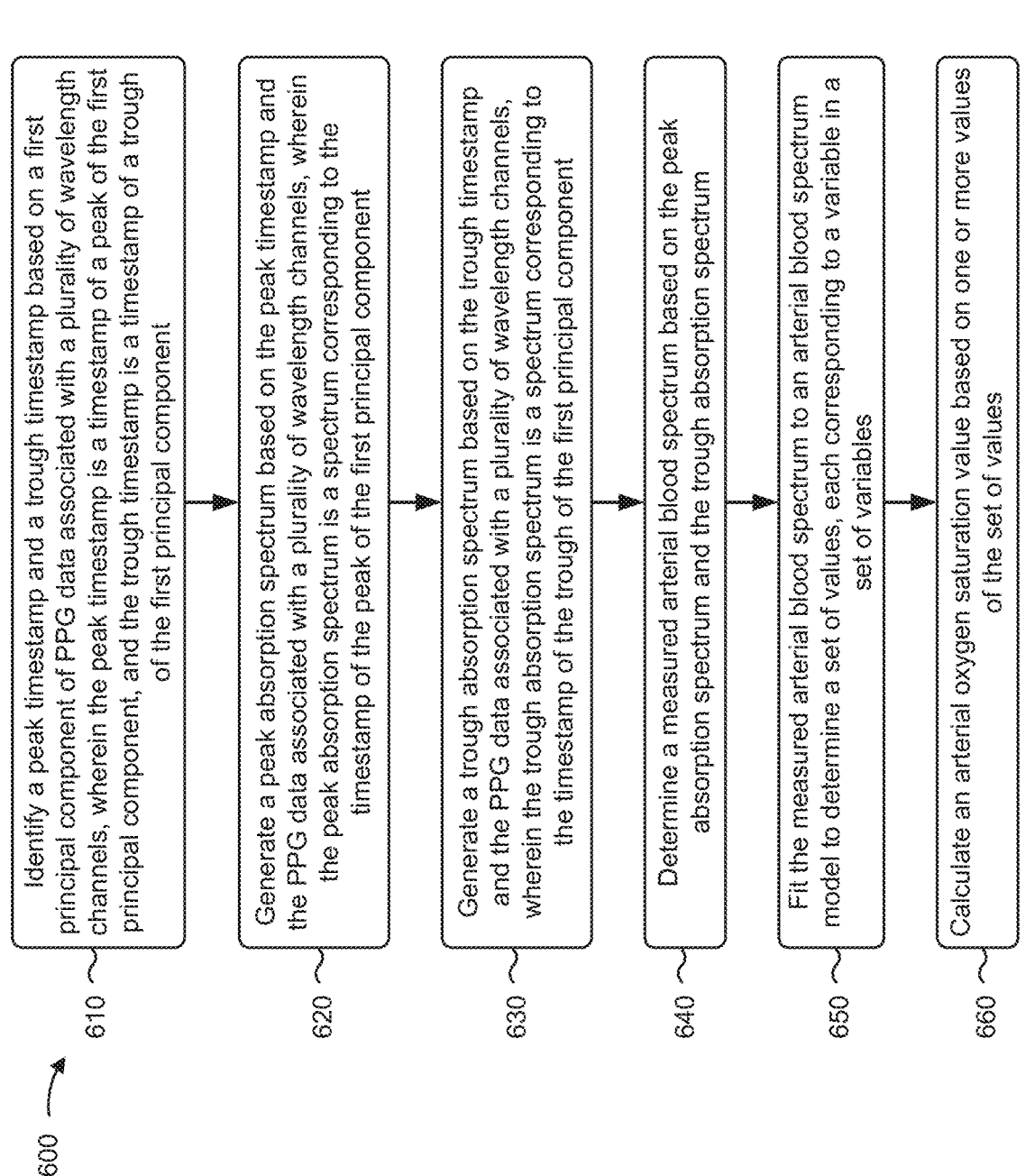

610  Identify a peak timestamp and a trough timestamp based on a first principal component of PPG data associated with a plurality of wavelength channels, wherein the peak timestamp is a timestamp of a peak of the first principal component, and the trough timestamp is a timestamp of a trough of the first principal component 620  Generate a peak absorption spectrum based on the peak timestamp and the PPG data associated with a plurality of wavelength channels, wherein the peak absorption spectrum is a spectrum corresponding to the timestamp of the peak of the first principal component 630  Generate a trough absorption spectrum based on the trough timestamp and the PPG data associated with a plurality of wavelength channels, wherein the trough absorption spectrum is a spectrum corresponding to the timestamp of the trough of the first principal component 640  Determine a measured arterial blood spectrum based on the peak absorption spectrum and the trough absorption spectrum 650  Fit the measured arterial blood spectrum to an arterial blood spectrum model to determine a set of values, each corresponding to a variable in a set of variables 660  Calculate an arterial oxygen saturation value based on one or more values of the set of values

CALIBRATION-FREE PULSE OXIMETRY

RELATED APPLICATION

This application is a continuation of U.S. patent application Ser. No. 16/780,412, filed Feb. 3, 2020 (now U.S. Pat. No. 11,331,017), which claims priority to U.S. Provisional Patent Application No. 62/805,173, filed on Feb. 13, 2019, and entitled "CALIBRATION-FREE PULSE OXIMETRY USING A BINARY MULTISPECTRAL SENSOR," the contents of which are incorporated herein by reference in their entireties.

BACKGROUND

Photoplethysmography (PPG) is an optical technique that can be used to detect volumetric changes in blood in peripheral circulation (as blood volume changes due to the pumping action of the heart). PPG is a non-invasive method that makes measurements at the surface of the skin (e.g., at a fingertip, a wrist, an ear lobe, and/or the like). A PPG device may take the form of, for example, a multispectral sensor device (e.g., a binary multispectral (BMS) sensor device) that provides PPG data associated with multiple wavelength channels (e.g., 64 wavelength channels). The multispectral sensor device may include multiple sensor elements (e.g., optical sensors, spectral sensors, and/or image sensors), each to receive one of the multiple wavelength channels (via a respective region of a multispectral filter) in order to capture the PPG data.

SUMMARY

According to some implementations, a method may include identifying, by a device, a peak timestamp and a trough timestamp based on a first principal component of PPG data associated with a plurality of wavelength channels, wherein the peak timestamp is a timestamp of a peak of the first principal component, and the trough timestamp is a timestamp of a trough of the first principal component; generating, by the device, a peak absorption spectrum based on the peak timestamp and the PPG data associated with the plurality of wavelength channels, wherein the peak absorption spectrum is a spectrum corresponding to the timestamp of the peak of the first principal component; generating, by the device, a trough absorption spectrum based on the trough timestamp and the PPG data associated with the plurality of wavelength channels, wherein the trough absorption spectrum is a spectrum corresponding to the timestamp of the trough of the first principal component; determining, by the device, a measured arterial blood spectrum based on the peak absorption spectrum and the trough absorption spectrum; fitting, by the device, an arterial blood spectrum model to the measured arterial blood spectrum to determine a set of values, each value in the set of values corresponding to a variable in a set of variables; and calculating, by the device, an arterial oxygen saturation value based on one or more values of the set of values.

According to some implementations, a device may include one or more memories; and one or more processors, communicatively coupled to the one or more memories, configured to: identify a peak timestamp and a trough timestamp based on a first principal component of PPG data associated with a plurality of wavelength channels, wherein the peak timestamp is a timestamp of a peak of the first principal component, and the trough timestamp is a timestamp of a trough of the first principal component; generate a peak absorption spectrum based on the peak timestamp and the PPG data associated with the plurality of wavelength channels, wherein the peak absorption spectrum is a spectrum corresponding to the timestamp of the peak of the first principal component; generate a trough absorption spectrum based on the trough timestamp and the PPG data associated with the plurality of wavelength channels, wherein the trough absorption spectrum is a spectrum corresponding to the timestamp of the trough of the first principal component; determine a measured arterial blood spectrum based on the peak absorption spectrum and the trough absorption spectrum; fit an arterial blood spectrum model to the measured arterial blood spectrum to determine a set of values, each value in the set of values corresponding to a variable in a set of variables; and calculate an arterial oxygen saturation value based on one or more values of the set of values.

According to some implementations, a non-transitory computer-readable medium may store one or more instructions. The one or more instructions, when executed by one or more processors of a device, may cause the one or more processors to: identify a peak timestamp and a trough timestamp based on a first principal component of PPG data associated with a plurality of wavelength channels, wherein the peak timestamp is a timestamp of a peak of the first principal component, and the trough timestamp is a timestamp of a trough of the first principal component; generate a peak absorption spectrum based on the peak timestamp and the PPG data associated with the plurality of wavelength channels, wherein the peak absorption spectrum is a spectrum corresponding to the timestamp of the peak of the first principal component; generate a trough absorption spectrum based on the trough timestamp and the PPG data associated with the plurality of wavelength channels, wherein the trough absorption spectrum is a spectrum corresponding to the timestamp of the trough of the first principal component; determine a measured arterial blood spectrum based on the peak absorption spectrum and the trough absorption spectrum; fit an arterial blood spectrum model to the measured arterial blood spectrum to determine a set of values, each value in the set of values corresponding to a variable in a set of variables; and calculate an arterial oxygen saturation value based on one or more values of the set of values.

BRIEF DESCRIPTION OF THE DRAWINGS

FIG. 6 is a flow chart of an example process for calculating an arterial oxygen saturation value using calibration-free pulse oximetry, as described herein.

DETAILED DESCRIPTION

Figures 1A, 1B:
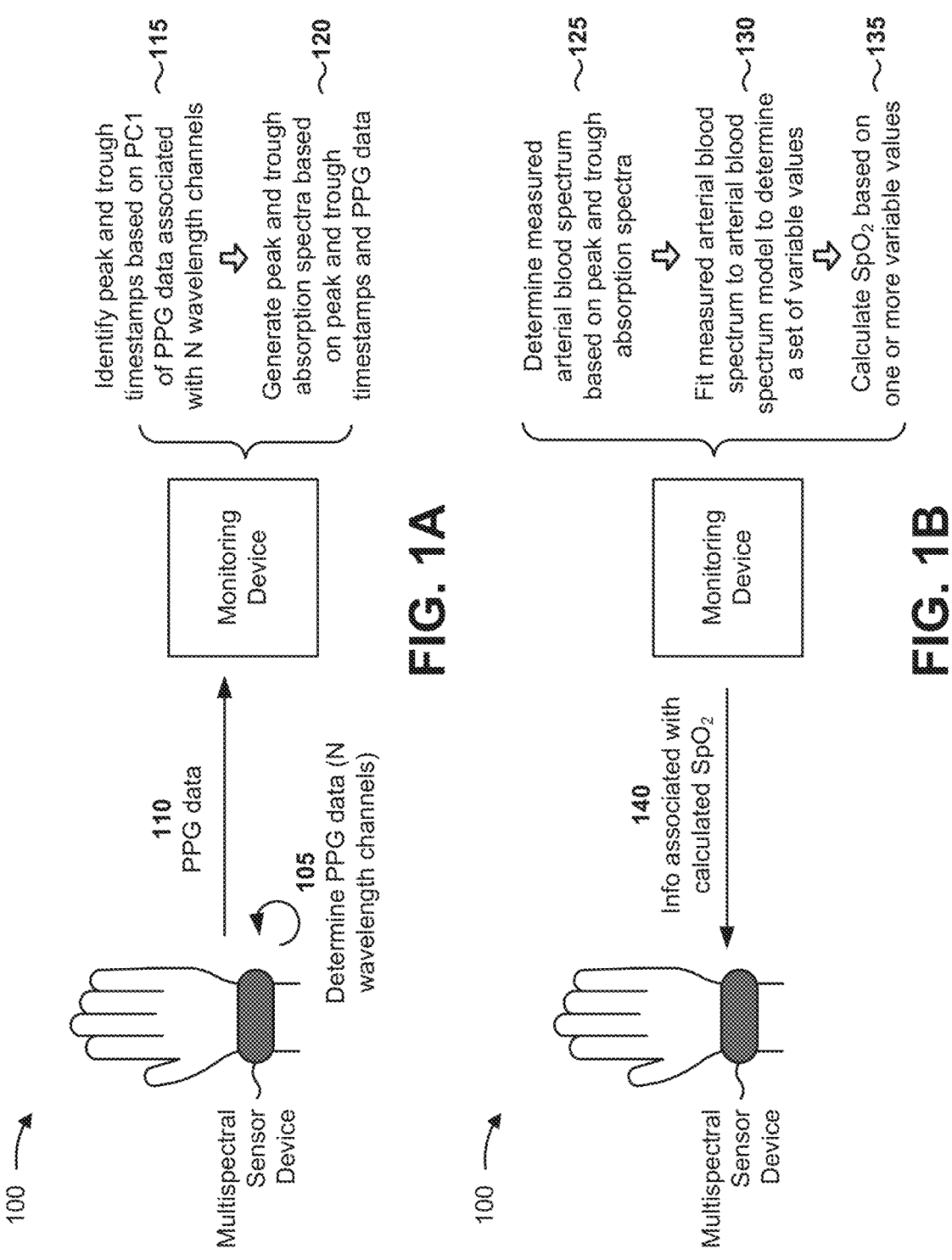
FIGS. 1A and 1B are diagrams of an example implementation described herein.

The following detailed description of example implementations refers to the accompanying drawings. The same reference numbers in different drawings may identify the same or similar elements. Further, while the following description may use a multispectral sensor device in an example, the principles, procedures, operations, techniques, and methods described herein may be used with any other type of sensing device, such as a spectrometer, an optical sensor, a spectral sensor, and/or the like.

Monitoring of arterial oxygen saturation can be achieved using a pulse oximeter. A conventional pulse oximeter uses two wavelengths of light (e.g., each generated by one of a respective pair of light emitting diodes (LEDs)), such as a wavelength in the red region and a wavelength in the infrared region. In operation, red and infrared absorbance are determined at both a peak and a trough of a PPG waveform. To relate optical absorbance of these wavelengths of light to arterial oxygen saturation, a manufacturer of a pulse oximeter must conduct human clinical studies to generate calibration curves for the pulse oximeter. These human clinical studies allow the manufacturer to determine an empirical calibration specific to the pulse oximeter (e.g., using a so-called "ratio of ratios" of the wavelength signals and measured oxygen levels), and this calibration equation can be used to provide measurements of arterial oxygen saturation using the pulse oximeter. Of course, human clinical studies required in order to provide calibration in this way can be expensive, complex, and/or time consuming. In addition to the cost, complexity, and time needed for such human studies, such human clinical studies may only collect data in the range of 70% to 100% arterial oxygen saturation. Thus, arterial oxygen saturation outside of the calibrated range cannot be measured. Further, arterial oxygen saturation for a person having unique physiological features (i.e., features that are not covered by the human subjects involved in the calibration process) cannot be accurately measured.

Some implementations described herein provide techniques and apparatuses for monitoring arterial oxygen saturation without a need for calibration of a device associated with monitoring arterial oxygen saturation. In some implementations, such calibration-free monitoring uses multichannel PPG data (e.g., 64 wavelength channels of PPG data) collected by a multispectral sensor device (e.g., a binary multispectral sensor (BMS)). Here, absorption spectra of arterial blood can be determined from the PPG data, and these absorption spectra can be fitted (e.g., in real-time or near real-time) to known spectra of oxygenated and deoxygenated hemoglobin, which enables calculation of arterial oxygen saturation.

Notably, the techniques and apparatuses described herein do not require human clinical studies that would otherwise be needed for providing a technique for calibration and, therefore, are more cost effective than a conventional pulse oximeter, and are also not limited by calibration conditions that would otherwise be associated with use of a calibration equation. Further, the techniques and apparatuses described herein may be used to measure arterial oxygen saturation for any subject, even a subject with unique physiological conditions (e.g., a subject who may not be represented in a calibration set constructed from "typical" individuals).

FIGS. 1A and 1B are diagrams of an example implementation 100 described herein.

As shown in FIG. 1A, a multispectral sensor device may be positioned relative to a skin surface of a subject. For example, as shown in FIG. 1A, the multispectral sensor device may be a device worn on the wrist of the subject. In some implementations, the multispectral sensor device may be positioned relative to the skin surface at another location on the body, such as on a fingertip, an arm, a leg, an ear lobe, and/or the like. In some implementations, the multispectral sensor device includes a BMS sensing device that operates in, for example, the visible (VIS) spectrum, the near infrared (NIR) spectrum, and/or the like. In some implementations, the multispectral sensor device may be capable of measuring, obtaining, collecting, or otherwise determining PPG data associated with multiple (e.g., 16, 32, 64, and/or the like) wavelength channels.

As shown by reference 105, the multispectral sensor device may determine (e.g., measure, gather, collect, and/or the like) PPG data (e.g., raw heartbeat data) associated with N (N>1) wavelength channels. The PPG data may include, for each of the N wavelength channels, photometric response data that indicates a blood volume beneath the skin surface at the location of the multispectral sensor device at a given time point.

As shown by reference 110, a monitoring device may obtain the PPG data from the multispectral sensor device. The monitoring device is a device capable of calculating arterial oxygen saturation from multi-channel PPG data, as described herein. In some implementations, the monitoring device may be integrated with the multispectral sensor device (e.g., in a same package, a same housing, on a same chip, and/or the like). Alternatively, the monitoring device may be separate (e.g., remotely located) from the multispectral sensor device.

In some implementations, the monitoring device may obtain the PPG data in real-time or near real-time (e.g., when the multispectral sensor device is configured to provide the PPG data as the multispectral sensor device obtains the PPG data). Additionally, or alternatively, the monitoring device may obtain the PPG data based on the multispectral sensor device (e.g., automatically) providing the PPG data on a periodic basis (e.g., every one second, every five seconds, and/or the like). Additionally, or alternatively, the monitoring device may obtain the PPG data from the multispectral sensor device based on requesting the PPG data from the multispectral sensor device.

As shown by reference 115, the monitoring device may identify a peak timestamp and a trough timestamp based on a first principal component (PC1) of the PPG data associated with the N wavelength channels. Here, the peak timestamp is a timestamp of a peak of a PC1 waveform, and the trough timestamp is a timestamp of a trough of the PC1 waveform (e.g., a trough of the PC1 waveform that is subsequent to the peak of the PC1 waveform). In some implementations, the peak timestamp and the trough timestamp may be referred to as a peak-trough timestamp pair.

Figure 2A:
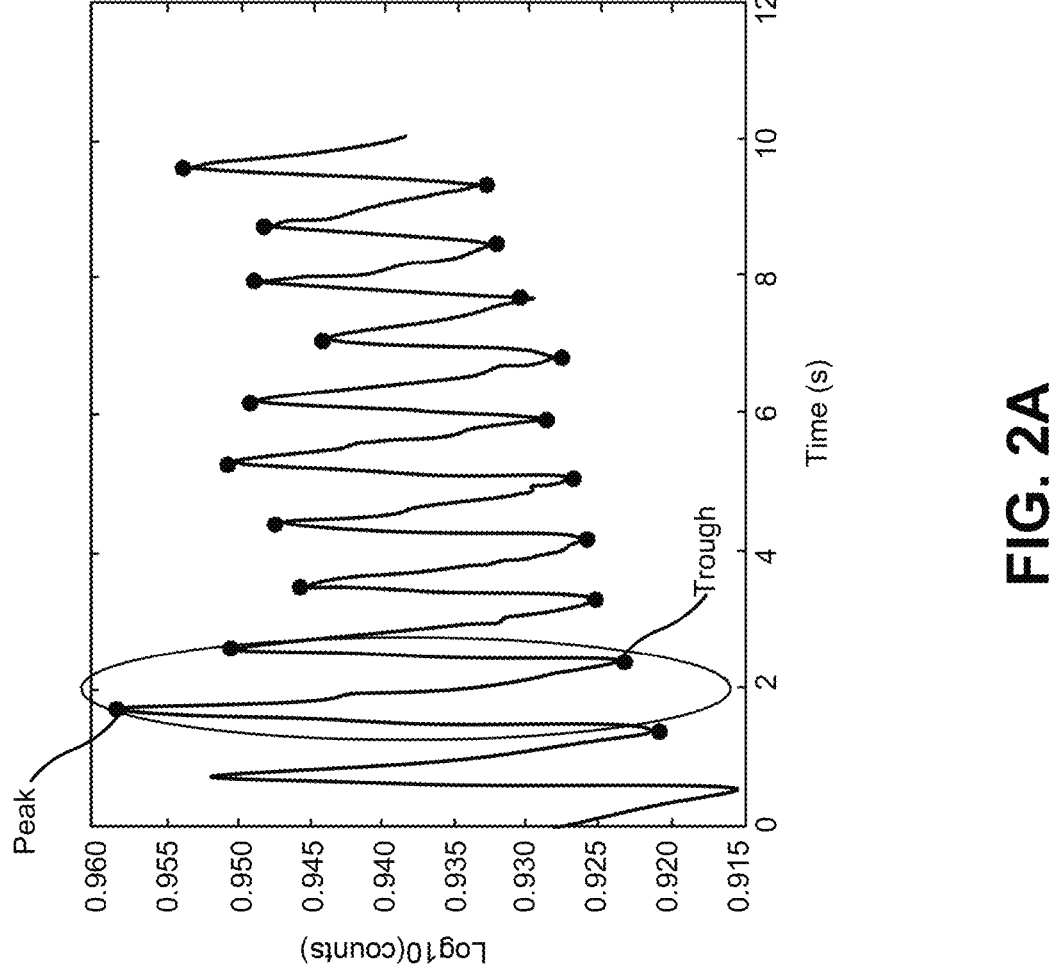
FIGS. 2A-2E are diagrams illustrating an example of calculating an arterial oxygen saturation value using calibration-free pulse oximetry, as described herein.

In some implementations, the monitoring device may determine PC1 of the PPG data. For example, the monitoring device may perform a principal component analysis (PCA) of the N wavelength channels by providing the N wavelength channels of PPG data as input to a PCA algorithm, where the PCA algorithm provides PC1 as an output. Here, PC1 is univariate time series data (i.e., single channel data) that defines a heartbeat profile. In general terms, the PCA acts to compress the multi-channel PPG data into univariate time series data (in the form of PC1). A waveform of an example of PC1 is shown in FIG. 2A, as described below.

Notably, PC1 may have a higher signal-to-noise ratio (SNR) than SNRs of individual wavelength channels and, therefore, may enable improved monitoring (e.g., as compared to using the multi-channel PPG data for monitoring). In some implementations, the monitoring device may determine PC1 after baseline correction of the N wavelength channels is performed and/or after one or more other preprocessing operations are performed on the N wavelength channels of PPG data. In some implementations, the monitoring device may determine PC1 in a manner described in U.S. patent application Ser. No. 16/210,740, filed on Dec. 8, 2018, and entitled "AUTONOMOUS FULL SPECTRUM BIOMETRIC MONITORING," the content of which is incorporated by reference herein in its entirety.

As shown by reference 120, the monitoring device may generate a peak absorption spectrum based on the peak timestamp and the PPG data associated with the plurality of wavelength channels, and may generate a trough absorption spectrum based on the trough timestamp and the PPG data associated with the plurality of wavelength channels. Here, the peak absorption spectrum is a spectrum corresponding to the timestamp of the peak of PC1, and the trough absorption spectrum is a spectrum corresponding to the timestamp of the trough of PC1.

Figure 2B:
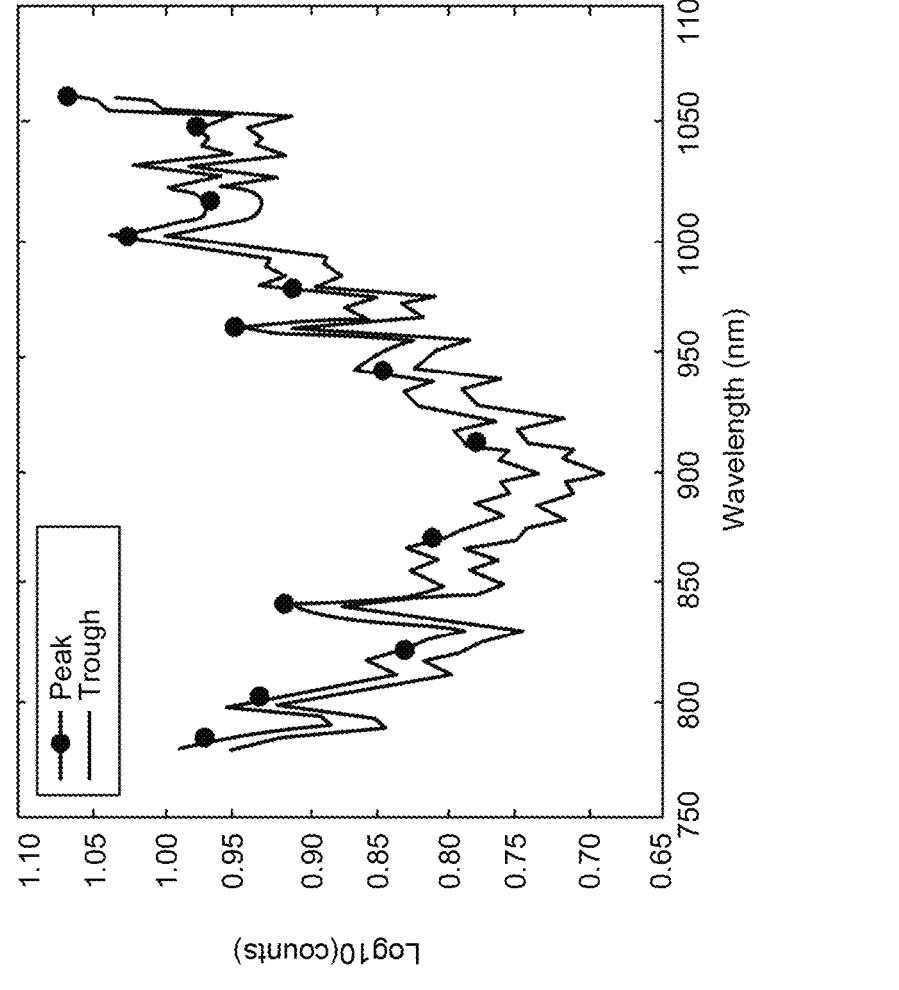

In some implementations, to generate the peak absorption spectrum, the monitoring device may determine a PPG response value for each of the N wavelength channels at a time identified by the timestamp of the peak of PC1. For example, referencing the PPG data for a first wavelength channel, the monitoring device may determine a PPG response value of the first wavelength channel at the time corresponding to the peak timestamp. Next, referencing the PPG data for a second wavelength channel, the monitoring device may determine a PPG response value of the second wavelength channel at the time corresponding to the peak timestamp. The monitoring device may perform this operation for each of the N wavelengths, and may generate the peak absorption spectrum accordingly. An example peak absorption spectrum is shown in FIG. 2B, as described below.

In some implementations, to generate the trough spectrum, the monitoring device may determine a PPG response value for each of the N wavelength channels at a time identified by the timestamp of the trough of PC1. For example, referencing the PPG data for a first wavelength channel, the monitoring device may determine a PPG response value of the first wavelength channel at the time corresponding to the trough timestamp. Next, referencing the PPG data for a second wavelength channel, the monitoring device may determine a PPG response value of the second wavelength channel at the time corresponding to the trough timestamp. The monitoring device may perform this operation for each of the N wavelengths, and may generate the trough absorption spectrum accordingly. An example trough absorption spectrum is shown in FIG. 2B, as described below.

Figure 2C:
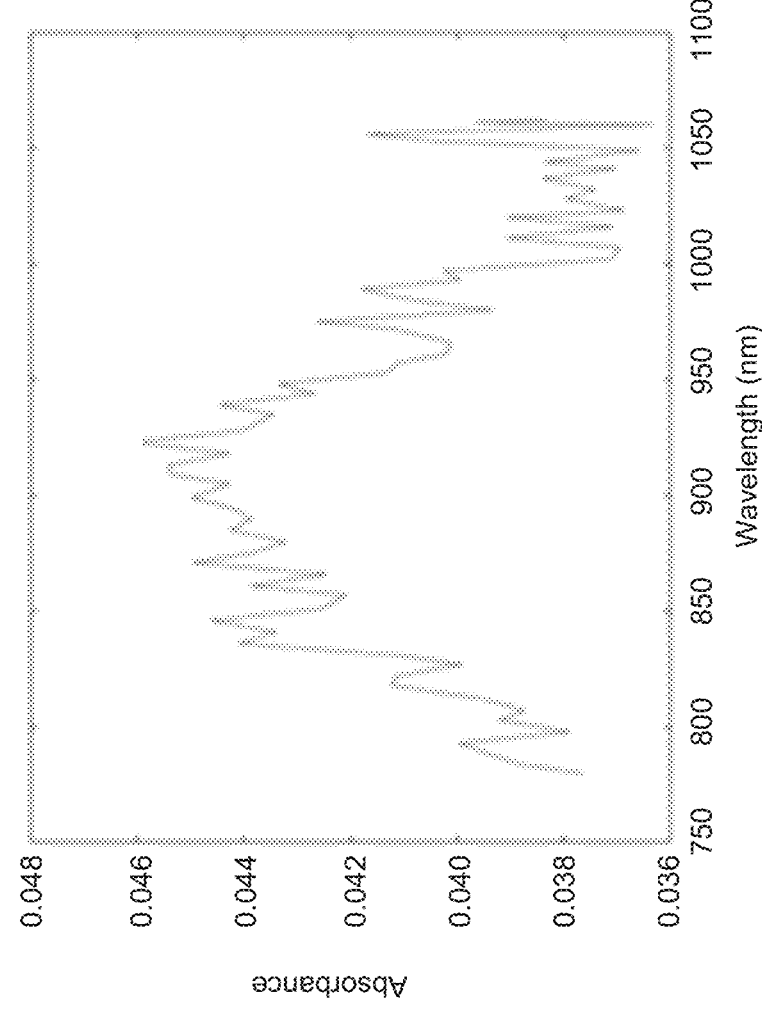

As shown by reference 125, the monitoring device may determine a measured arterial blood spectrum based on the peak absorption spectrum and the trough absorption spectrum. In some implementations, the monitoring device may determine the measured arterial blood spectrum based at least in part on subtracting the trough absorption spectrum from the peak absorption spectrum. Here, a result of subtracting the trough absorption spectrum from the peak absorption spectrum is the measured arterial blood spectrum. An example of a measured arterial blood spectrum is shown in FIG. 2C, as described below.

In some implementations, the monitoring device may smooth the measured arterial blood spectrum prior to fitting an arterial blood spectrum model to the measured arterial blood spectrum (as described below). In some implementations, smoothing of the measured arterial blood spectrum may be performed using a conventional smoothing technique.

In some implementations, the monitoring device may cut the measured arterial blood spectrum prior to fitting an arterial blood spectrum model to the measured arterial blood spectrum (as described below). For example, the monitoring device may select a portion of the measured arterial blood spectrum associated with a particular wavelength range for fitting of the arterial blood spectrum model, and fit the arterial blood spectrum model to the portion of the measured arterial blood spectrum associated with the particular wavelength range (rather than fitting the arterial blood spectrum model to the entire measured arterial blood spectrum). In some implementations, the particular wavelength range may be configurable on the monitoring device (e.g., such that a wavelength range known to provide an accurate arterial oxygen saturation value in a given application can be configured for use by the monitoring device).

Figure 2D:
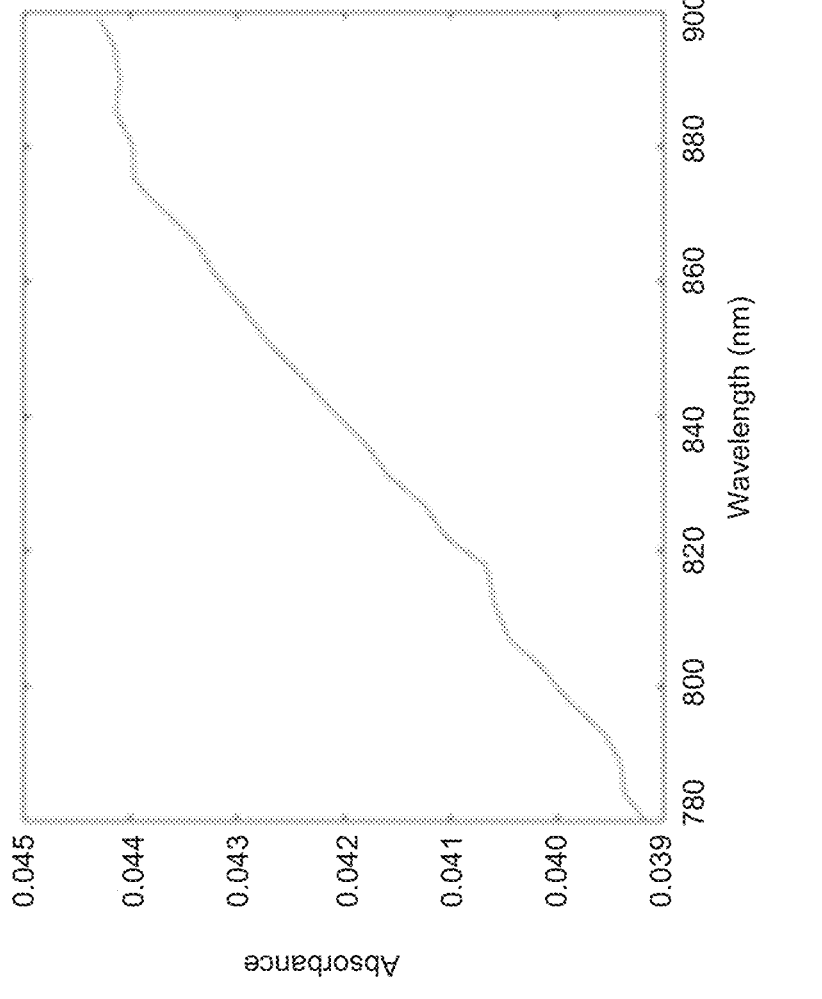

In some implementations, the monitoring device may both smooth and cut the measured arterial blood spectrum prior to fitting the arterial blood spectrum model to the measured arterial blood spectrum. An example of a smoothed and cut measured arterial blood spectrum is shown in FIG. 2D, as described below.

As shown by reference 130, the monitoring device may fit an arterial blood spectrum model to the measured arterial blood spectrum. In some implementations, fitting of the arterial blood spectrum model includes determining a set of variable values (e.g., a set of values, each of which corresponds to a variable in a set of variables) associated with the arterial blood spectrum model. In some implementations, the monitoring device may fit the arterial blood spectrum model to the measured arterial blood spectrum after smoothing and/or cutting the measured arterial blood spectrum, as described above.

In some implementations, the arterial blood spectrum model may be a model that allows oxygen absorption by arterial blood to be approximated. For example, the arterial blood spectrum model may be a Taylor expansion attenuation model described by a formula of the form:

$$A_{model}(\lambda)=c_0+c_1\lambda+\langle L\rangle\,[c_{Hb}\varepsilon_{Hb}(\lambda)+c_{HbO_2}\varepsilon_{HbO_2}(\lambda)]+c_{H_2O}\varepsilon_{H_2O}(\lambda) \qquad (1)$$

where $A_{model}(\lambda)$ is oxygen absorption by arterial blood, $c_0$ and $c_1$ are constants, (L) is a mean pathlength of reflected light through the arterial blood, $\varepsilon_{Hb}(\lambda)$ is a wavelength-dependent extinction coefficient for deoxygenated hemoglobin, $\varepsilon_{HbO_2}(\lambda)$ is a wavelength-dependent extinction coefficient for oxygenated hemoglobin, $\varepsilon_{H_2O}(\lambda)$ is a wavelength-dependent extinction coefficient for water, $c_{Hb}$ is a concentration of deoxygenated hemoglobin, $c_{HbO_2}$ is a concentration of oxygenated hemoglobin, and $c_{H_2O}$ is a concentration of water. The term $c_1\lambda$ describes scattering from the tissue, and the term $c_{H_2O}\varepsilon_{H_2O}(\lambda)$ describes water absorption, where the pathlength attributable to water absorption is merged with the estimation of water fraction (to simplify calculation). In the Taylor expansion attenuation model, there are six variables for which values are unknown: $c_0$, $c_1$, $\langle L\rangle$, $c_{Hb}$, $c_{HbO_2}$, and $c_{H_2O}$.

In some implementations, to fit the arterial blood spectrum model to the measured arterial blood spectrum, the monitoring device may obtain a set of initial values for each of the six variables (e.g., the monitoring device may determine initial guesses for values of the six variables), and may fit the arterial blood spectrum model to the measured arterial blood spectrum based on the set of initial values. In some implementations, the monitoring device may obtain the set of initial values using a simulated annealing technique.

Figure 2E:
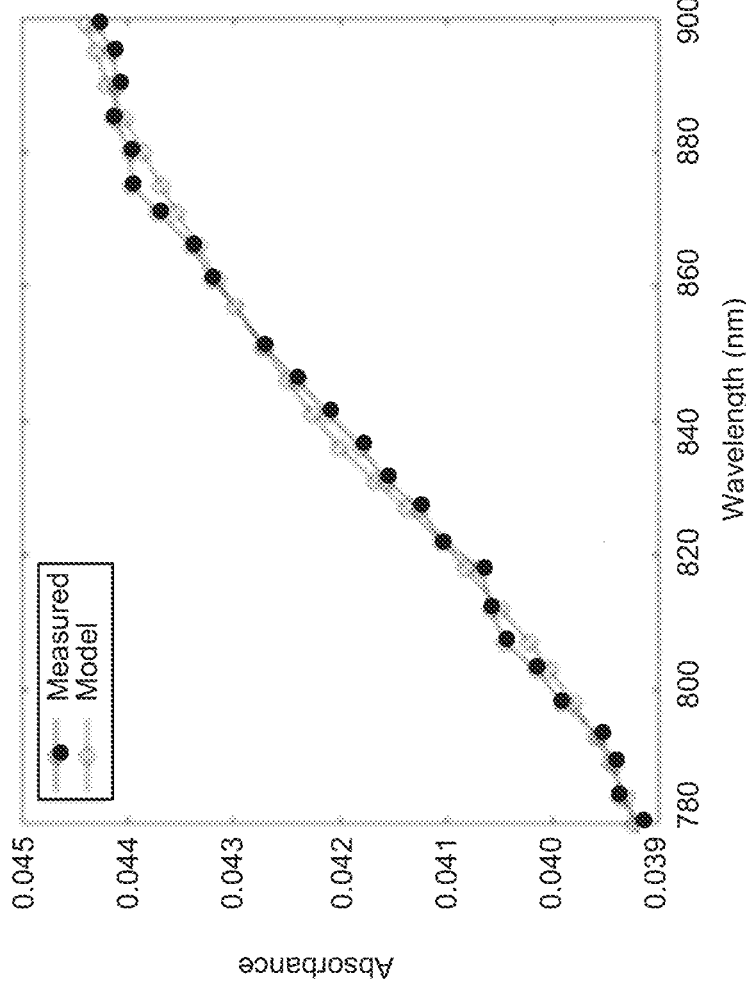

In some implementations, the monitoring device may fit the arterial blood spectrum model to the measured arterial blood spectrum by minimizing a sum of squared differences between a modeled arterial blood spectrum and the measured arterial blood spectrum with a nonlinear least square method. Here, when the sum of squared differences between the modeled arterial blood spectrum and the measured arterial blood spectrum is minimized, the monitoring device has determined values for the above set of variables ($c_0$, $c_1$, $\langle L \rangle$, $C_{Hb}$, $c_{HbO_2}$ and $c_{H_2O}$). An example of an arterial blood spectrum model after fitting to a measured arterial blood spectrum is shown in FIG. 2E, as described below.

Notably, the Taylor expansion attenuation model is provided as an example of a model that can be used for approximation of oxygen absorption by arterial blood, and other models describing oxygen absorption by the arterial blood can be fitted in a similar manner.

As shown by reference 135, the monitoring device may calculate an arterial oxygen saturation value based on one or more values of the set of values determined by fitting the arterial blood spectrum model to the measured arterial blood spectrum. In some implementations, the monitoring device may calculate the arterial oxygen saturation based on one or more values determined by fitting of the arterial blood spectrum model to the measured arterial blood spectrum. For example, in some implementations, the monitoring device may calculate the arterial oxygen saturation value ($SpO_2$) using a formula of the form:

$$SpO_2 = \frac{C_{HbO_2}}{C_{HbO_2} + C_{Hb}} \times 100\% \tag{2}$$

where $c_{Hb}$ and $c_{HbO_2}$ are the values as determined by fitting of the arterial blood spectrum model to the measured arterial blood spectrum in the manner described above.

In some implementations, as shown by reference 140, the monitoring device may provide information associated with the arterial oxygen saturation value. For example, in some implementations, the monitoring device may provide information that identifies the arterial oxygen saturation value for display (e.g., via a display screen of the multispectral sensor device, via a display screen of the monitoring device, and/or the like).

In some implementations, the monitoring device may repeat the above described process (e.g., automatically on a periodic basis, based on an indication of a user, and/or the like) in order to enable monitoring of arterial oxygen saturation (e.g., in real-time or near real-time).

In this way, a monitoring device can monitor arterial oxygen saturation without a need for calibration of a device associated with monitoring arterial oxygen saturation. That is, the monitoring device may provide arterial oxygen saturation monitoring without a need for human clinical studies that would otherwise be needed for generating a calibration equation and, therefore, the monitoring device is more cost effective than a conventional pulse oximeter. Further, monitoring of arterial oxygen saturation by the monitoring device is not limited by calibration conditions that would otherwise be associated with use of a calibration equation.

As indicated above, FIGS. 1A and 1B are provided merely as examples. Other examples may differ from what is described with regard to FIGS. 1A and 1B.

FIGS. 2A-2E are diagrams illustrating an example of calculating an arterial oxygen saturation value using calibration-free pulse oximetry, as described herein.

FIG. 2A is a diagram of an example waveform of a PC1 of PPG data associated with a plurality of wavelength channels. In some implementations, the monitoring device may identify a peak timestamp and a trough timestamp (e.g., a trough timestamp immediately following the peak timestamp) based on a waveform such as that shown in FIG. 2A, as described above. In FIG. 2A, peaks and troughs are indicated by black dots, and in this example the monitoring device identifies timestamps of the peak and trough indicated by the oval shown in FIG. 2A.

Next, the monitoring device may generate peak and trough absorption spectra, as described above. FIG. 2B is a diagram of an example of peak and trough absorption spectra generated based on the peak and trough timestamps identified in FIG. 2A, and the PPG data associated with the plurality of wavelength channels. As shown in FIG. 2B, the monitoring device may generate a peak absorption spectrum for the plurality of wavelength channels (e.g., ranging from approximately 780 nanometers (nm) to approximately 1050 nm), and may generate trough absorption spectra for the plurality of wavelength channels.

Next, the monitoring device may determine a measured arterial blood spectrum based on the peak absorption spectrum and the trough absorption spectrum, as described above. FIG. 2C is a diagram of an example of a measured arterial blood spectrum generated from the peak and trough absorption spectra shown in FIG. 2B. In some implementations, the monitoring device may generate the measured arterial blood spectrum based at least in part on subtracting the trough absorption spectrum from the peak absorption spectrum, as described above.

Next, the monitoring device may determine to smooth and cut the measured arterial blood spectrum, as described above. FIG. 2D is a diagram of an example of a smoothed and cut portion of the measured arterial blood spectrum shown in FIG. 2C. In the example shown in FIG. 2D, the measured arterial blood spectrum is smoothed and cut such as to cover a portion of the original wavelength (e.g., a wavelength range from 780 nm to 900 nm).

Next, the monitoring device may fit an arterial blood spectrum model to the measured arterial blood spectrum to determine a set of values, as described above. FIG. 2E is a diagram of an example illustrating an arterial blood spectrum model after fitting to a measured arterial blood spectrum. In some implementations, one or more values determined as a result of fitting the arterial blood spectrum model to the measured arterial blood spectrum may then be used to calculate an arterial oxygen saturation value, as described above.

As indicated above, FIGS. 2A-2E are provided merely as examples. Other examples may differ from what is described with regard to FIGS. 2A-2E.

Figure 3:
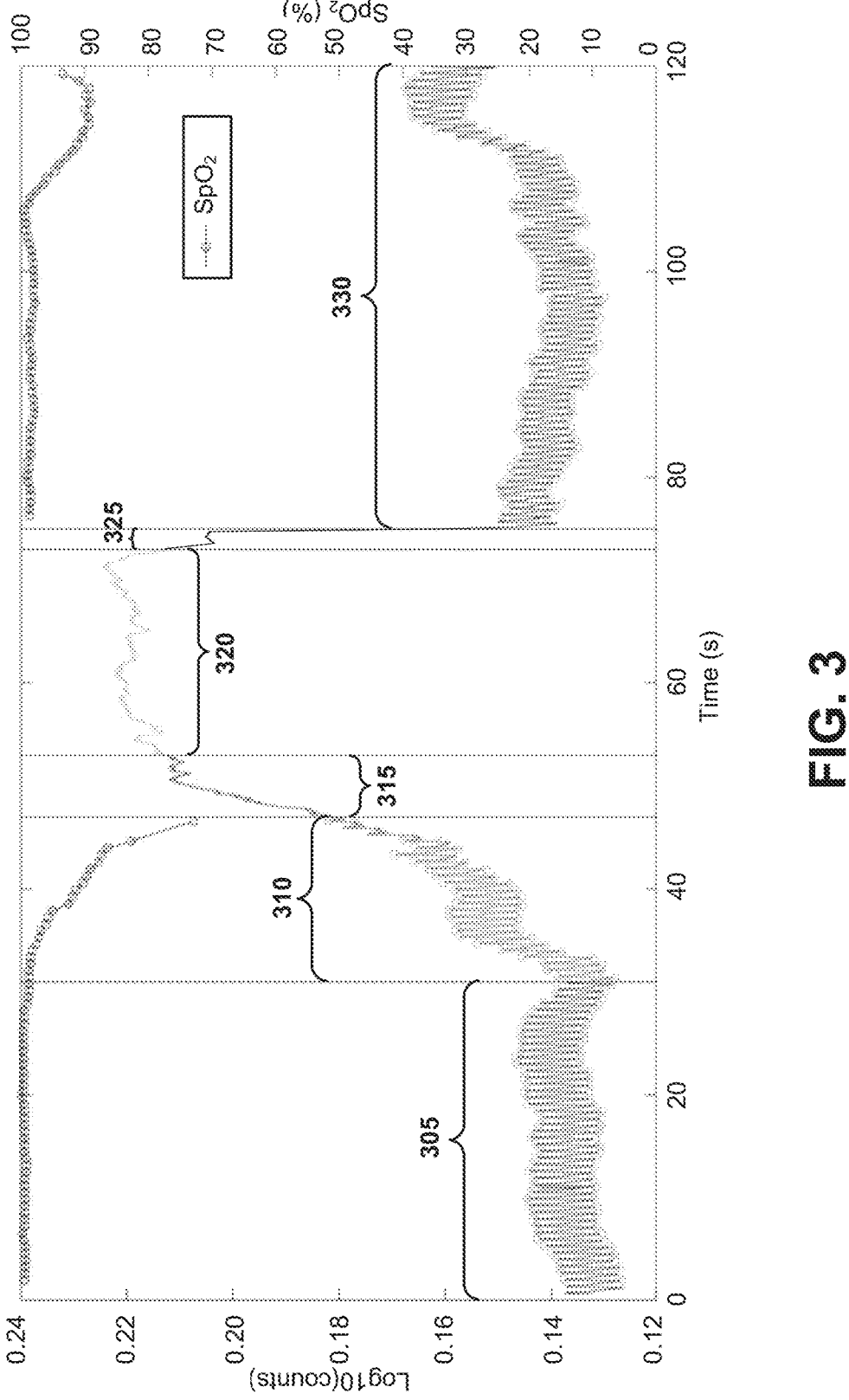
FIG. 3 is a diagram illustrating an example proof of concept of calculating an arterial oxygen saturation value using calibration-free pulse oximetry, as described herein.

FIG. 3 is a diagram illustrating an example proof of concept of calculating an arterial oxygen saturation value using calibration-free pulse oximetry, as described herein. In association with generating FIG. 3, an arterial occlusion test was conducted to monitor changes of arterial oxygen saturation over time by restricting blood flow to an arm of a subject using a sphygmomanometer to apply an external pressure that was greater than a systolic blood pressure of the subject. During this arterial occlusion test, the external pressure was applied twice for approximately 30 seconds each time. Here, signals were collected from a forefinger of a left hand of the subject. Notably, for a healthy human subject, arterial oxygen saturation values should be in a range from approximately 94% to approximately 100% when blood flow is not restricted, and should decrease when blood flow is restricted.

In FIG. 3, the waveform labeled with reference numbers in the 300s is a PPG waveform (at 798 nm) during the arterial occlusion test, while the line labeled as "SpO$_2$" identifies arterial oxygen saturation values calculated in the manner described above.

The portion of the PPG waveform labeled with reference 305 is the PPG waveform during a time period before the external pressure was applied to the subject. As shown, arterial oxygen saturation values during this time period are in the expected normal range (e.g., from approximately 94% to approximately 100%).

The portion of the PPG waveform labeled with reference 310 is the PPG waveform during a time period while the external pressure is being applied, but before the external pressure reaches a target pressure (e.g., a pressure that is 20 millimeters of Mercury (mmHg) higher the subject's systolic blood pressure, which is a pressure at which blood supply is expected to be completely restricted). As shown, arterial oxygen saturation values during this time period begin to decrease, as expected (e.g., since blood flow is being increasingly restricted during this time period).

The portion of the PPG waveform labeled with reference 315 is the PPG waveform during a time period while the external pressure has reached the target pressure. As indicated, arterial oxygen saturation values during this time period has decreased dramatically, as expected, (e.g., since blood flow is completely restricted during this time period) and should be minimized during this time period. The portion of the PPG waveform labeled with reference 320 is the PPG waveform during a time period at which the external pressure is held at the target pressure. As indicated, arterial oxygen saturation values during this time period remain at a minimal level (e.g., since blood flow is completely restricted). The portion of the PPG waveform labeled with reference 325 is the PPG waveform during a time period while the external pressure is being released. As indicated, arterial oxygen saturation values during this time period remain minimized, but may begin to increase (e.g., since blood flow is being increasingly unrestricted during this time period). Notably, at the portions of the PPG waveform labeled with references 315, 320, and 325 (e.g., from a time at which the external pressure has reached the target pressure to a time after which the external pressure has been released), the waveform is damped such that peaks and troughs are not separable. Thus, arterial oxygen saturation values may not be calculable. During the time period of reference 325, although the pressure was released, there is a delay for the PPG waveform to show separable peaks and troughs.

The portion of the PPG waveform labeled with reference 330 is the PPG waveform during a time period after the external pressure has been released. As shown, arterial oxygen saturation values during this time period return to the expected normal range.

As indicated above, FIG. 3 is provided merely as an example. Other examples may differ from what is described with regard to FIG. 3.

Figure 4:
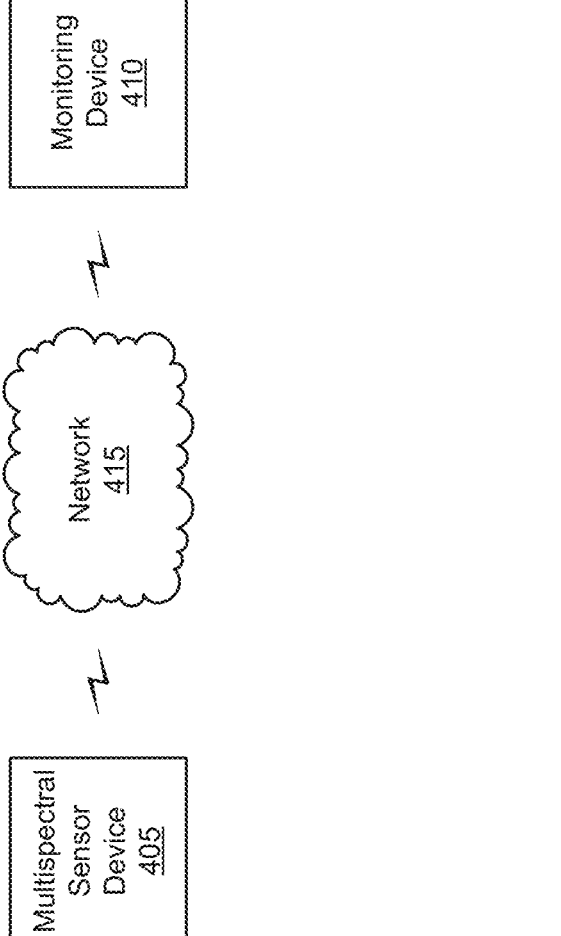
FIG. 4 is a diagram of an example environment in which systems and/or methods described herein may be implemented.

FIG. 4 is a diagram of an example environment 400 in which systems and/or methods described herein may be implemented. As shown in FIG. 4, environment 400 may include a multispectral sensor device 405, a monitoring device 410, and a network 415. Devices of environment 400 may interconnect via wired connections, wireless connections, or a combination of wired and wireless connections.

Multispectral sensor device 405 includes a device capable of measuring, gathering, collecting, or otherwise determining PPG data associated with a plurality of wavelength channels, as described herein. For example, multispectral sensor device 405 may include a multispectral sensor device capable of determining PPG data (in the form of multivariate time-series data) on each of 64 wavelength channels. In some implementations, multispectral sensor device 405 may operate in the visible spectrum, the near infrared spectrum, the infrared spectrum, and/or the like. In some implementations, multispectral sensor device 405 may be a wearable device (e.g., a device worn that can be worn on a wrist, a finger, an arm, a leg, a head, an ear, and/or the like). In some implementations, multispectral sensor device 405 may be integrated with monitoring device 410 (e.g., such that multispectral sensor device 405 and monitoring device 410 are on the same chip, in the same package, in the same housing, and/or the like). Alternatively, in some implementations, multispectral sensor device 405 may be separate from monitoring device 410. In some implementations, multispectral sensor device 405 may receive information from and/or transmit information to another device in environment 400, such as monitoring device 410.

Monitoring device 410 includes a device capable of performing one or more operations associated with calculating an arterial oxygen saturation value using calibration-free pulse oximetry, as described herein. For example, monitoring device 410 may include an application specific integrated circuit (ASIC), an integrated circuit, a server, a group of servers, and/or the like, and/or another type of communication and/or computing device. In some implementations, monitoring device 410 may be integrated with multispectral sensor device 405 (e.g., such that multispectral sensor device 405 and monitoring device 410 are on the same chip, in the same package, in the same housing, and/or the like). Alternatively, in some implementations, monitoring device 410 may be separate from multispectral sensor device 405. In some implementations, monitoring device 410 may receive information from and/or transmit information to another device in environment 400, such as multispectral sensor device 405.

Network 415 includes one or more wired and/or wireless networks. For example, network 415 may include a wired network (e.g., when multispectral sensor device 405 and monitoring device 410 are included in a same package and/or a same chip). As another example, network 415 may include a cellular network (e.g., a long-term evolution (LTE) network, a code division multiple access (CDMA) network, a 3G network, a 4G network, a 5G network, another type of next generation network, etc.), a public land mobile network (PLMN), a local area network (LAN), a wide area network (WAN), a metropolitan area network (MAN), a telephone network (e.g., the Public Switched Telephone Network (PSTN)), a private network, an ad hoc network, an intranet, the Internet, a fiber optic-based network, a cloud computing network, or the like, and/or a combination of these or other types of networks.

The number and arrangement of devices and networks shown in FIG. 4 are provided as an example. In practice, there may be additional devices and/or networks, fewer devices and/or networks, different devices and/or networks, or differently arranged devices and/or networks than those shown in FIG. 4. Furthermore, two or more devices shown in FIG. 4 may be implemented within a single device, or a single device shown in FIG. 4 may be implemented as multiple, distributed devices. Additionally, or alternatively, a set of devices (e.g., one or more devices) of environment

400 may perform one or more functions described as being performed by another set of devices of environment 400.

Figure 5:
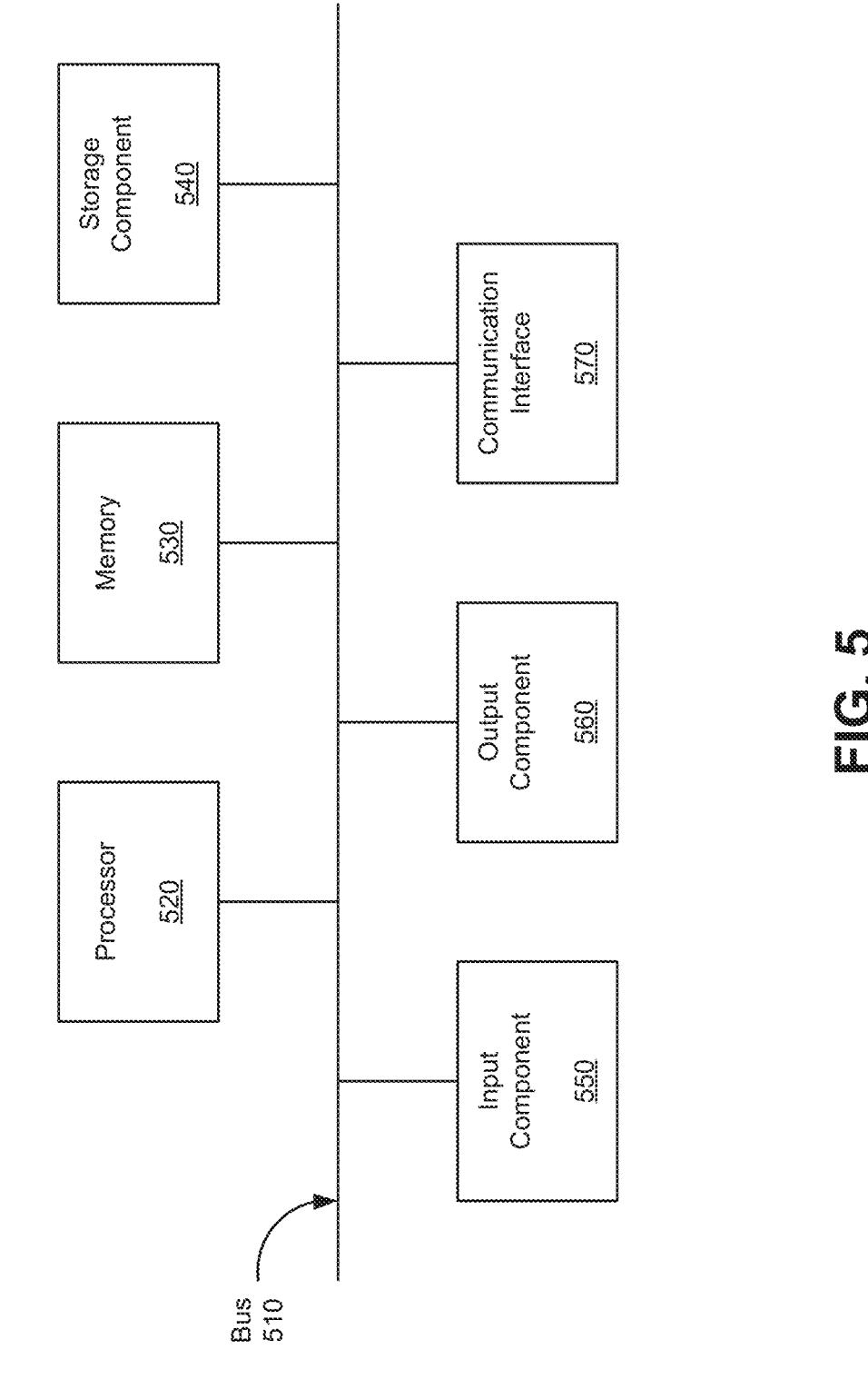
FIG. 5 is a diagram of example components of one or more devices of FIG. 4.

FIG. 5 is a diagram of example components of a device 500. Device 500 may correspond to multispectral sensor device 1005 and/or monitoring device 1010. In some implementations, multispectral sensor device 1005 and/or monitoring device 1010 may include one or more devices 500 and/or one or more components of device 500. As shown in FIG. 5, device 500 may include a bus 510, a processor 520, a memory 530, a storage component 540, an input component 550, an output component 560, and a communication interface 570.

Bus 510 includes a component that permits communication among multiple components of device 500. Processor 520 is implemented in hardware, firmware, and/or a combination of hardware and software. Processor 520 is a central processing unit (CPU), a graphics processing unit (GPU), an accelerated processing unit (APU), a microprocessor, a microcontroller, a digital signal processor (DSP), a field-programmable gate array (FPGA), an application-specific integrated circuit (ASIC), or another type of processing component. In some implementations, processor 520 includes one or more processors capable of being programmed to perform a function. Memory 530 includes a random access memory (RAM), a read only memory (ROM), and/or another type of dynamic or static storage device (e.g., a flash memory, a magnetic memory, and/or an optical memory) that stores information and/or instructions for use by processor 520.

Storage component 540 stores information and/or software related to the operation and use of device 500. For example, storage component 540 may include a hard disk (e.g., a magnetic disk, an optical disk, and/or a magneto-optic disk), a solid state drive (SSD), a compact disc (CD), a digital versatile disc (DVD), a floppy disk, a cartridge, a magnetic tape, and/or another type of non-transitory computer-readable medium, along with a corresponding drive.

Input component 550 includes a component that permits device 500 to receive information, such as via user input (e.g., a touch screen display, a keyboard, a keypad, a mouse, a button, a switch, and/or a microphone). Additionally, or alternatively, input component 550 may include a component for determining location (e.g., a global positioning system (GPS) component) and/or a sensor (e.g., an accelerometer, a gyroscope, an actuator, another type of positional or environmental sensor, and/or the like). Output component 560 includes a component that provides output information from device 500 (via, e.g., a display, a speaker, a haptic feedback component, an audio or visual indicator, and/or the like).

Communication interface 570 includes a transceiver-like component (e.g., a transceiver, a separate receiver, a separate transmitter, and/or the like) that enables device 500 to communicate with other devices, such as via a wired connection, a wireless connection, or a combination of wired and wireless connections. Communication interface 570 may permit device 500 to receive information from another device and/or provide information to another device. For example, communication interface 570 may include an Ethernet interface, an optical interface, a coaxial interface, an infrared interface, a radio frequency (RF) interface, a universal serial bus (USB) interface, a Wi-Fi interface, a cellular network interface, and/or the like.

Device 500 may perform one or more processes described herein. Device 500 may perform these processes based on processor 520 executing software instructions stored by a non-transitory computer-readable medium, such as memory

530 and/or storage component 540. As used herein, the term "computer-readable medium" refers to a non-transitory memory device. A memory device includes memory space within a single physical storage device or memory space spread across multiple physical storage devices.

Software instructions may be read into memory 530 and/or storage component 540 from another computer-readable medium or from another device via communication interface 570. When executed, software instructions stored in memory 530 and/or storage component 540 may cause processor 520 to perform one or more processes described herein. Additionally, or alternatively, hardware circuitry may be used in place of or in combination with software instructions to perform one or more processes described herein. Thus, implementations described herein are not limited to any specific combination of hardware circuitry and software.

The number and arrangement of components shown in FIG. 5 are provided as an example. In practice, device 500 may include additional components, fewer components, different components, or differently arranged components than those shown in FIG. 5. Additionally, or alternatively, a set of components (e.g., one or more components) of device 500 may perform one or more functions described as being performed by another set of components of device 500.

FIG. 6 is a flow chart of an example process 600 for calculating an arterial oxygen saturation value using calibration-free pulse oximetry. In some implementations, one or more process blocks of FIG. 6 may be performed by a monitoring device (e.g., monitoring device 410). In some implementations, one or more process blocks of FIG. 6 may be performed by another device or a group of devices separate from or including the device, such as a multispectral sensor device (e.g., multispectral sensor device 405), and/or the like.

As shown in FIG. 6, process 600 may include identifying a peak timestamp and a trough timestamp based on a first principal component of PPG data associated with a plurality of wavelength channels (block 610). For example, the monitoring device (e.g., using processor 520, memory 530, storage component 540, input component 550, output component 560, communication interface 570 and/or the like) may identify a peak timestamp and a trough timestamp based on a first principal component of PPG data associated with a plurality of wavelength channels, as described above. In some implementations, the peak timestamp is a timestamp of a peak of the first principal component, and the trough timestamp is a timestamp of a trough of the first principal component.

As further shown in FIG. 6, process 600 may include generating a peak absorption spectrum based on the peak timestamp and the PPG data associated with the plurality of wavelength channels (block 620). For example, the monitoring device (e.g., using processor 520, memory 530, storage component 540, input component 550, output component 560, communication interface 570 and/or the like) may generate a peak absorption spectrum based on the peak timestamp and the PPG data associated with the plurality of wavelength channels, as described above. In some implementations, the peak absorption spectrum is a spectrum corresponding to the timestamp of the peak of the first principal component.

As further shown in FIG. 6, process 600 may include generating a trough absorption spectrum based on the trough timestamp and the PPG data associated with the plurality of wavelength channels (block 630). For example, the monitoring device (e.g., using processor 520, memory 530, storage component 540, input component 550, output component 560, communication interface 570 and/or the like) may generate a trough absorption spectrum based on the trough timestamp and the PPG data associated with the plurality of wavelength channels, as described above. In some implementations, the trough absorption spectrum is a spectrum corresponding to the timestamp of the trough of the first principal component.

As further shown in FIG. 6, process 600 may include determining a measured arterial blood spectrum based on the peak absorption spectrum and the trough absorption spectrum (block 640). For example, the monitoring device (e.g., using processor 520, memory 530, storage component 540, input component 550, output component 560, communication interface 570 and/or the like) may determine a measured arterial blood spectrum based on the peak absorption spectrum and the trough absorption spectrum, as described above.

As further shown in FIG. 6, process 600 may include fitting the arterial blood spectrum model to the measured arterial blood spectrum to determine a set of values, each value in the set of values corresponding to a variable in a set of variables (block 650). For example, the monitoring device (e.g., using processor 520, memory 530, storage component 540, input component 550, output component 560, communication interface 570 and/or the like) may fit an arterial blood spectrum model to the measured arterial blood spectrum to determine a set of values, each value in the set of values corresponding to a variable in a set of variables, as described above.

As further shown in FIG. 6, process 600 may include calculating an arterial oxygen saturation value based on one or more values of the set of values (block 660). For example, the monitoring device (e.g., using processor 520, memory 530, storage component 540, input component 550, output component 560, communication interface 570 and/or the like) may calculate an arterial oxygen saturation value based on one or more values of the set of values, as described above.

Process 600 may include additional implementations, such as any single implementation or any combination of implementations described below and/or in connection with one or more other processes described elsewhere herein.

In some implementations, process 600 includes smoothing the measured arterial blood spectrum prior to fitting the arterial blood spectrum model to the measured arterial blood spectrum.

In some implementations, process 600 includes selecting a portion of the measured arterial blood spectrum associated with a particular wavelength range for fitting of the arterial blood spectrum model. Here, fitting the arterial blood spectrum model to the measured arterial blood spectrum comprises fitting the arterial blood spectrum model to the portion of the measured arterial blood spectrum associated with the particular wavelength range.

In some implementations, the measured arterial blood spectrum is determined based at least in part on subtracting the trough absorption spectrum from the peak absorption spectrum.

In some implementations, the set of values is determined based on minimizing a sum of squared differences between a spectrum associated with the arterial blood spectrum model and the measured arterial blood spectrum using a non-linear least square method.

In some implementations, process 600 includes obtaining a set of initial values for each variable of the set of variables using a simulated annealing technique. Here, fitting the arterial blood spectrum model to the measured arterial blood spectrum comprises fitting the arterial blood spectrum model to the measured arterial blood spectrum using the set of initial values.

In some implementations, the arterial blood spectrum model is a Taylor expansion attenuation model.

In some implementations, the set of variables includes a variable corresponding to a concentration of deoxygenated hemoglobin and a variable corresponding to a concentration of oxygenated hemoglobin, and the one or more values based on which the arterial oxygen saturation is calculated include a value of the variable corresponding to the concentration of deoxygenated hemoglobin and a value of the variable corresponding to the concentration of oxygenated hemoglobin.

In some implementations, process 600 includes providing information associated with the arterial oxygen saturation value.

Although FIG. 6 shows example blocks of process 600, in some implementations, process 600 may include additional blocks, fewer blocks, different blocks, or differently arranged blocks than those depicted in FIG. 6. Additionally, or alternatively, two or more of the blocks of process 600 may be performed in parallel.

Some implementations described herein provide techniques and apparatuses for monitoring arterial oxygen saturation without a need for calibration of a device associated with monitoring arterial oxygen saturation. In some implementations, such calibration-free monitoring uses multi-channel PPG data (e.g., 64 wavelength channels of PPG data) collected by a multispectral sensor device (e.g., a BMS). In some implementations, absorption spectra of arterial blood can be determined from the PPG data, and these absorption spectra can be fitted (e.g., in real-time or near real-time) to known spectra of oxygenated and deoxygenated hemoglobin, which enables calculation of arterial oxygen saturation.

The foregoing disclosure provides illustration and description, but is not intended to be exhaustive or to limit the implementations to the precise forms disclosed. Modifications and variations may be made in light of the above disclosure or may be acquired from practice of the implementations.

As used herein, the term "component" is intended to be broadly construed as hardware, firmware, and/or a combination of hardware and software.

As used herein, satisfying a threshold may, depending on the context, refer to a value being greater than the threshold, more than the threshold, higher than the threshold, greater than or equal to the threshold, less than the threshold, fewer than the threshold, lower than the threshold, less than or equal to the threshold, equal to the threshold, or the like.

It will be apparent that systems and/or methods described herein may be implemented in different forms of hardware, firmware, or a combination of hardware and software. The actual specialized control hardware or software code used to implement these systems and/or methods is not limiting of the implementations. Thus, the operation and behavior of the systems and/or methods are described herein without reference to specific software code—it being understood that software and hardware can be designed to implement the systems and/or methods based on the description herein.

Even though particular combinations of features are recited in the claims and/or disclosed in the specification, these combinations are not intended to limit the disclosure of various implementations. In fact, many of these features may be combined in ways not specifically recited in the claims and/or disclosed in the specification. Although each dependent claim listed below may directly depend on only one claim, the disclosure of various implementations includes each dependent claim in combination with every other claim in the claim set.

No element, act, or instruction used herein should be construed as critical or essential unless explicitly described as such. Also, as used herein, the articles "a" and "an" are intended to include one or more items, and may be used interchangeably with "one or more." Further, as used herein, the article "the" is intended to include one or more items referenced in connection with the article "the" and may be used interchangeably with "the one or more." Furthermore, as used herein, the term "set" is intended to include one or more items (e.g., related items, unrelated items, a combination of related and unrelated items, etc.), and may be used interchangeably with "one or more." Where only one item is intended, the phrase "only one" or similar language is used. Also, as used herein, the terms "has," "have," "having," or the like are intended to be open-ended terms. Further, the phrase "based on" is intended to mean "based, at least in part, on" unless explicitly stated otherwise. Also, as used herein, the term "or" is intended to be inclusive when used in a series and may be used interchangeably with "and/or," unless explicitly stated otherwise (e.g., if used in combination with "either" or "only one of").

What is claimed is:

1. A method comprising:
   determining, by a multispectral sensor device, photoplethysmography (PPG) data associated with a plurality of wavelength channels;
   providing, by the multispectral sensor device, the PPG data; and
   identifying, by the multispectral sensor device and based on providing the PPG data, an arterial oxygen saturation value that is based on minimizing a sum of squared differences between a modeled arterial blood spectrum and a measured arterial blood spectrum using a nonlinear least square method, and
   wherein the measured arterial blood spectrum is based on the PPG data.

2. The method of claim 1, wherein the PPG data includes, for a channel of the plurality of wavelength channels, photometric response data that indicates a blood volume beneath a skin surface at a location of the multispectral sensor device at a given time point.

3. The method of claim 1, wherein the multispectral sensor device is positioned relative to a skin surface of a subject.

4. The method of claim 1, wherein the multispectral sensor device is a wearable device.

5. The method of claim 1, wherein providing the PPG data comprises:
   providing the PPG data to a monitoring device that is separate from the multispectral sensor device.

6. The method of claim 1, further comprising:
   receiving, from a monitoring device that is separate from the multispectral sensor device, the information associated with the arterial oxygen saturation value.

7. The method of claim 1, wherein providing the PPG data comprises:
   providing the PPG data to a monitoring device in real-time or near real-time to determining the PPG data.

8. The method of claim 1, further comprising:
   receiving a request from a monitoring device.

9. A multispectral sensor device, comprising:
   one or more memories; and
   one or more processors, coupled to the one or more memories, configured to:
   determine photoplethysmography (PPG) data associated with a plurality of wavelength channels;
   provide the PPG data; and
   identify an arterial oxygen saturation value,
      wherein the arterial oxygen saturation value is based on minimizing a sum of squared differences between a modeled arterial blood spectrum and a measured arterial blood spectrum, and
      wherein the measured arterial blood spectrum is based on the PPG data.

10. The multispectral sensor device of claim 9, wherein the PPG data includes, for a channel of the plurality of wavelength channels, photometric response data that indicates a blood volume beneath a skin surface at a location of the multispectral sensor device at a given time point.

11. The multispectral sensor device of claim 9, wherein the multispectral sensor device is positioned relative to a skin surface of a subject.

12. The multispectral sensor device of claim 9, wherein the multispectral sensor device is a wearable device.

13. The multispectral sensor device of claim 9, wherein the one or more processors, to provide the PPG data, are configured to:
   provide the PPG data to a monitoring device that is separate from the multispectral sensor device.

14. The multispectral sensor device of claim 9, wherein the one or more processors are further configured to:
   receive, from a monitoring device that is separate from the multispectral sensor device, the information associated with the arterial oxygen saturation value.

15. The multispectral sensor device of claim 9, wherein the one or more processors, to provide the PPG data, are configured to:
   provide the PPG data to a monitoring device in real-time or near real-time to determining the PPG data.

16. The multispectral sensor device of claim 9, wherein the one or more processors are further configured to:
   receive a request from a monitoring device,
      wherein the one or more processors, to provide the PPG data, are configured to:
      provide the PPG data to the monitoring device based on receiving the request.

17. A non-transitory computer-readable medium storing a set of instructions, the set of instructions comprising:
   one or more instructions that, when executed by one or more processors of a multispectral sensor device, cause the multispectral sensor device to:
   determine photoplethysmography (PPG) data associated with a plurality of wavelength channels;
   provide the PPG data; and
   identify an arterial oxygen saturation value,
      wherein the arterial oxygen saturation value is based on a modeled arterial blood spectrum and a measured arterial blood spectrum, and
      wherein the measured arterial blood spectrum is based on the PPG data.

18. The non-transitory computer-readable medium of claim 17, wherein the PPG data includes, for a channel of the plurality of wavelength channels, photometric response data that indicates a blood volume beneath a skin surface at a location of the multispectral sensor device at a given time point.

19. The non-transitory computer-readable medium of claim 17, wherein the multispectral sensor device is positioned relative to a skin surface of a subject.

20. The non-transitory computer-readable medium of claim 17, wherein the one or more instructions, that cause the multispectral sensor device to provide the PPG data, cause the multispectral sensor device to:

provide the PPG data to a monitoring device that is separate from the multispectral sensor device.

* * * * *